United States Patent [19]

Audibert et al.

[11] 4,125,603

[45] Nov. 14, 1978

[54] STABILIZED WATER-IN-OIL EMULSIONS AND COMPOSITIONS

[75] Inventors: Francoise Audibert, Neuilly-sur-Seine; Edgar Lederer, Sceaux; Louis Chedid, Paris, all of France

[73] Assignee: Agence Nationale de Valorisation de la Recherche (ANVAR), Neuilly-sur-Seine, France

[21] Appl. No.: 656,738

[22] Filed: Feb. 9, 1976

[30] Foreign Application Priority Data

Feb. 7, 1975 [FR] France ................................ 75 04003

[51] Int. Cl.$^2$ ..................... A61K 39/02; A61K 39/04; A61K 47/00
[52] U.S. Cl. ........................................ 424/88; 424/89; 424/92; 424/359; 424/360; 424/365

[58] Field of Search ................... 424/89, 88, 359, 365, 424/92, 360

[56] References Cited

U.S. PATENT DOCUMENTS

| 1,890,860 | 12/1932 | Omohundro | 424/359 |
| 3,435,117 | 3/1969 | Nichols | 424/359 |
| 3,469,003 | 9/1969 | Hardy | 424/89 |

*Primary Examiner*—Sam Rosen
*Attorney, Agent, or Firm*—Weiser, Stapler & Spivak

[57] ABSTRACT

Stabilized water-in-oil emulsions containing metabolizable vegetable oil, water in a quantity less than the oil and a non-immunogenic stabilizing protein in a quantity suitable to ensure the stability of the emulsion. Compositions which contain such an emulsion and a water soluble adjuvant and/or a vaccinating antigen in solution or suspension in the emulsion. A kit containing the above.

32 Claims, No Drawings

STABILIZED WATER-IN-OIL EMULSIONS AND COMPOSITIONS

The present invention relates to new compositions which permit the administration, in an effective and readily tolerated form, of immunological adjuvants capable of stimulating in a host immunizing responses to antigens of various kinds, to adjuvant preparations making use of these compositions and to processes for obtaining these adjuvant preparations. It relates especially to preparations which enable the efficient and readily tolerated administration of adjuvant agents which reinforce and enhance the action of the weak immunogens which may be used for the immunization of man and warm-blooded animals against bacterial, viral and parasitic infections and against various tissue antigens of normal or pathological origin especially against those which are the origin of tumors. Finally, it relates more particularly to vaccine preparations containing such adjuvant agents in addition to the vaccinating antigen proper of these vaccine preparations.

Numerous agents which are effective as immunological adjuvants have already described in the literature. The best known are the adjuvants of Freund: namely (a) the incomplete adjuvant of Freund which is based on mineral oil (for example the mineral oil known as "Bayol F"), containing an emulsifier (mannitol monooleate) known as "Arlacel"; and (b) the complete adjuvant of Freund which has the same composition as the first but includes dead mycobacteria. In the latter, all the mycobacteria may be replaced by purified cell walls or liposoluble fractions such as wax D. Water-soluble adjuvant agents have recently been described which may also be obtained from mycobacteria, or even other bacteria. Finally, there have been described still more recently adjuvant agents which have been obtained by synthesis.

The adjuvant action of the adjuvants of the Freund type which are based on a mineral oil and Arlacel requires that they be made up into an emulsion of one part of an oily phase to one part of an aqueous phase. The use of Arlacel is indispensable and the proportions of aqueous to oily phase are essential.

In spite of their high adjuvant power, such preparations however cannot be used in practice on account of the aggression shown by a non-metabolisable agent, the lack of innocuousness of the emulsifying agent and, for the complete adjuvant, the immunopathological effects manifested in this composition by certain mycobacterial preparations.

The substitution of a metabolizable vegetable oil for the mineral oil in the incomplete adjuvant of Freund, without any other modification, cannot be envisaged, since then stable emulsions are not obtained. Certain attempts at the stabilisation of such emulsions have been considered, but, at the cost of large proportions of emulsifying agents or stabilisers which are difficultly acceptable on account of their lack of innocuousness.

The object of the invention is to remove these disadvantages and to provide an emulsifiable or emulsified composition in which all the constituents are, without exception, non-toxic and readily metabolizable, while enabling the immunological adjuvants strongly to carry out their adjuvant action with regard to the vaccinating antigens, especially the weak immunogens capable of being used for the immunisation of man or animal.

According to the present invention a water-in-oil emulsion is provided, the principal constituents of which are a metabolizable vegetable oil and water, the emulsion containing less water than oil, in particular between about 2 and 6 volumes of water to 10 volumes of the vegetable oil, and also containing especially in dissolved form in the aqueous phase, protein in a quantity adapted to ensure the stability of the emulsion.

Preferably it contains between about 2.5 and 5 volumes of water, especially of the order of 3 volumes of water to 10 volumes of the vegetable oil.

The invention is based on the discovery that it is posible to obtain a very stable water-in-oil emulsion from a vegetable oil and water, in the presence of protein as the sole stabilizing agent, provided that the proportions of oil used are distinctly greater than those of the water.

The non-adherence to this last condition, that is the use of equal volumes of these two constituents to make a water-in-oil emulsion, does not allow the production of a stable emulsion in the presence of protein alone.

It is therefore remarkable that, by a modification of the proportions of only the water and the oil, it is possible, in the absence of any other stabilizing agents well known in this field, especially Arlacel, to produce a stable emulsion.

When the emulsion in question has to serve as a vehicle for a medicament, it is, of course, proper that the proteins used should not be immunogen with regard to the host for which the medicament is intended. In this latter case, there is then obtained an emulsion of which all the constituents are metabolizable.

The proportions of protein which must be used vary within a fairly wide range. They comprise in general between about 30 mg and about 150 mg, preferably between about 40 mg and about 120 mg, for example, 60 mg of protein per ml of aqueous phase of the emulsion.

Taken in these proportions, the protein provides for the stability of the final emulsion. They may also be sufficient to confer on the medium the isotonic character required for injection into man or animal. However, if need be, one could have recourse to a supplementary addition of a suitable agent to provide this isotonicity to the medium, especially sodium chloride or glucose, in the proportions required to obtain this isotonicity.

The origin of the vegetable oil used is of no importance to the level of stability of the emulsion. Analogous results are obtained when an oil according to the French Pharmacopia 8th Ed., 1965 p. 574–581 is used, in particular, groundnut or olive oil, for example, or other oils, for example sesame oils.

in the same way, when the emulsion is intended to serve as a vehicle for an active principle of a medicament, all proteins which are non-immunogenic with respect to the host can be called on, preferably proteins of human or animal origin, according to whether the medicament is intended for man or animal. For example, these proteins could consist of serum albumin or globulin extracts of human or animal blood, of the plasma or placenta, these proteins being able to be kept in aqueous medium.

The enulsions thus obtained constitute a preferred medium for the active principles of vaccines, and more still for adjuvant agents of non-specific immunity. It has been found that these active principles of vaccines, and more still the adjuvant agents, are capable of better exercising their activity when they are administered to the host in the emulsion according to the invention. In particular, the efficiency of the stimulation of the immunizing responses in the host by the adjuvant agents is of the same order of magnitude when they are administered in suspension in the incomplete adjuvant of Freund. This activity is all the more remarkable in that the administration of the adjuvant agent in this form is not accompanied in practice by the disadvantages mentioned above, in connection with the Freund adjuvant.

It is to be noted that the "water-in-oil" character of the emulsions according to the invention is important with respect to the part they are called upon to play within the scope of the preferred application of the invention. In particular, it is important that these emulsions should be stable, even in the presence of an aqueous phase, especially in situations of the type that they are called upon to meet in he organisms in which they are introduced, with an adjuvant agent and, preferably also, a vaccinating antigen or the like. In particular, it is important that the droplets of water in suspension in the oily phase of the water-in-oil emulsion should have no tendency to escape therefrom immediately when this emulsion is put in contact with an aqueous phase. This stability appears to be at the base of the undoubtedly necessary retard diffusion of the active principles introduced into the organism, in order to permit them to be captured by the competent immunological systems, for example the macrophages or the ganglions.

The invention therefore also relates to a medicament containing as the active principle an adjuvant agent of the kind in question, preferably associated with a vaccinating antigen, the active principle being associated with an emulsion of the type defined above.

A preferred adjuvant agent consists of an oligomer poor in neutral sugars or free from the latter and whose monomeric unit contains amino-sugars and amino-acids of the polymers constituting the cell walls of the Mycobacteria or the cells of Nocardia. Processes for obtaining such adjuvant agents have been described in U.S. patent application Ser. No. 307,614 issued as U.S. Pat. No. 4,036,953 on July 17, 1977, of which copending application Ser. No. 806,987 is a divisional application. and in U.S. patent application Ser. No. 371,512, now issued as U.S. Pat. No. 3,976,544 to Chedid et al on Aug. 24, 1976.

Other preferred adjuvant agents consist of soluble fragments of peptidoglycan taking part in the constitution of cell walls of procaryotes, especially oligosaccharides-oligopeptides, formed from N-acetyl-glucosamine units, N-acylmuramic acid units, in which the acyl group is preferably of the glycolyl or acetyl type, and tripeptide, tetrapeptide, heptapeptide groups formed in particular from L-alanine, D-glutamic acid, meso-$\alpha\xi$-diaminopimelic acid and D-alanine, such agents having been described particularly in copending U.S. patent application Ser. No. 516,991. They have also been the object of publication in "Biochemical and Biophysical Research Communications", 1974, Vol. 56 No. 3.561–567.

Others again are constituted by a compound formed from a N-acyl-muramic acid, to which is linked a short peptide chain containing at least two amino-acids, and in which the acyl group is formed from a glycolyl or acetyl group and in which the short peptide chain comprises a first amino-acid attached to the N-acyl-muramic acid, constituted by L-alanine and a second amino-acid constituted by D-glutamic acid, the carboxyl functions of this second amino acid being, individually, either free, or aminated (in the case of a peptide chain only carrying two amino-acids), or engaged in a linkage with another amino acid (in the case of a longer peptide chain), such adjuvant agents having also been described in U.S. patent application Ser. No. 516,991 referred to above.

Among these adjuvant agents, it is suitable to mention N-acetyl-muramyl dipeptide, of which the dipeptide contains the L-alanine and D-glutamic acid, more exactly N-acetyl-muramyl-L-alanyl-D-isoglutamine. The adjuvant activity of this compound has been described in "Biochemical and Biophysical Research Communications", 1974, Vol 59, No. 4 1317–1325.

Other adjuvant agents are constituted by the liposoluble preparations isolated from *Mycobacterium tuberculosis,* for example wax D or cord factor extracts of Peurois strain.

The adjuvant preparations thus obtained in emulsion form are very stable. In the tests which have been carried out, preparations of this type have kept their stability at the end of three months storage.

Making an emulsion of such compositions is moreover extremely easy. It may be effected extemporaneously from the constituents which have been indicated above and in the proportions which have been stated, by simple mixing and, directly in the syringe, serving for the administration of the preparation to the host.

The invention also relates to the presentations or "kits" containing the quantities or volumes of the various constituents predetermined as a function of the proportions which have been defined above and in bottles or analogous receptacles, so that the user can simply mix them and produce the emulsion, for the purpose of obtaining a composition directly ready for use.

The invention therefore relates more particularly to a presentation or "kit" of a liquid injectable vehicle formed from:
  water or physiological serum,
  vegetable oil,
  non-immunogenic proteins
in which these various constituents are provided in bottles or receptacles, which are separate or not, in volumes or weights which are predetermined as a function of the proportions defined above, with a view to the extemporaneous formation of an emulsion.

This kit also preferably includes active medicament principles essentially constituted by a vaccinating antigen or by an adjuvant of non-specific immunity, or by both at once, if necessary separated from one another, each of these active principles also being able to be grouped with one or other of the aforesaid constituents of the emulsion.

For example such a kit can comprise (1) an ampule containing a metabolizable vegetable oil, a second ampule containing protein, especially human or animal protein in lyophilized state, and a third ampule containing an aqueous physiological serum, or (2) an ampule containing the vegetable oil and a second ampule containing human or animal protein in solution in the physiological serum. In the two kits the adjuvant agent and the active principle of the vaccine are able either to be contained in separate ampules, or to be incorporated, for example, in one or other of the aforesaid ampules, as they are more compatible with water or oil, more soluble in water or oil.

Examples of tests are described below, in particular those which enable one to determine the relative proportions of the various constituents necessary for a stable emulsion from the constituents which have been defined above.

The test carried out to find the stability of the emulsion is obtained by observing the adherence of the emulsion to the walls of the inverted container and, better still, by depositing a drop of this emulsion on the surface of water, according to the technique described by W. J. Herbert in the "Handbook of Experimental Immunology", D. W. Weir ed., Blackwell Scientific Publications Oxford and Edinburgh, 1967, 1211, under the title "Methods for the preparation of water-in-oil, and multiple, emulsions for use as antigen adjuvants; and notes on their use in immunization procedures". When the emulsion is not stable, the drop disintegrates by separation of the two phases.

(1) Conditions for obtaining a stable water-in-oil emulsion (a) A study of the water-vegetable oil proportions of the emulsion: comparison between the incomplete adjuvant of Freund (mineral oil) and an emulsion according to the invention based on groundnut oil.

If an aqueous solution containing 60 mg/ml of bovine serum-albumin (SAB) is taken and 10 volumes of this solution are put in a mixer of the POTTER type, to which are added 10 volumes of oil and the mixture is emulsified at 2000 rpm for 1 minute, a good emulsion is obtained, as usual, with the mineral oil but an emulsion is not observed with the vegetable oil. On the contrary, under the same conditions, if 3 volumes of the solution of SAB are put in 10 volumes of oil, a good emulsion is observed in the vegetable oil and no emulsion in the mineral oil.

This experiment is repeated by adding systematically to 10 volumes of groundnut oil 1, 1.5, 2, 2.5, 3, 4, 5, 6, 7, 8, 9 or 10 volumes of water containing 60 mg/ml of SAB. As may be seen from the following Table, an emulsion is obtained in the vegetable oil on condition the ratio 6/10 is not exceeded, preferably 5/10. The optimum of effect and of stability is obtained when the proportions are 3/10.

| Production and stability of the emulsion as a function of the ratio of water to oil | | | | | | | | | | | | |
|---|---|---|---|---|---|---|---|---|---|---|---|---|
| N° of volumes of aqueous solution of SAB* added to 10 volumes of groundnut oil | 1 | 1.5 | 2 | 2.5 | 3 | 4 | 5 | 6 | 7 | 8 | 9 | 10 |
| production of an emulsion | — | — | — | + | + | + | ± | — | — | — | — | — |
| Stability of the emulsion | | | | ± | + | ± | — | | | | | |

*Aqueous solution having 60 mg/ml of SAB.

On the contrary, with the mineral oil, it is necessary to comply with the proportion 10/10. Results analogous to those of the groundnut oil are obtained if olive oil, according to the FRENCH Pharmacopia 1965, 8th Edition, or sesame oil is used. No effect is observed for proportions above 5/10, the optimum being at 3/10 for olive oil and 2.5/10 for sesame oil.

(b) Effect of the protein content of the aqueous solution.

In the experiments which are described below, 1 volume of water containing the SAB is always added to 3 volumes of groundnut oil. The content of SAB in the water varies between 15% and 0%. It is seen from the following Table that stable emulsions are obtained when the content of protein varies between 4% and 12%. Below 4% and above 12% the emulsions obtained are not stable.

| Production and stability of the emulsion as a function of the content of proteins of the aqueous solution (ratio:water/oil = ⅓). | | | | | | | | | | | |
|---|---|---|---|---|---|---|---|---|---|---|---|
| SAB (%) in aqueous solution) | 0 | 0.25 | 0.5 | 1 | 2 | 3 | 4 | 6 | 8 | 10 | 12 | 15 |
| Production of the emulsion | — | — | — | — | ± | + | + | + | + | + | + | + |
| stability of the emulsion | | | | | — | — | + | + | + | + | + | — |

Analogous results can be obtained by using human serum albumin (SAH) or serum proteins of mice.

It must also be noted that, contrary to what is observed with the Freund adjuvants, the emulsions in vegetable oils do not require the presence of Arlacel. The presence of this product in the emulsion according to the invention is useless, even unfavourable.

The preceding results demonstrate that it is possible to obtain a stable water-in-oil vegetable emulsion provided that well defined proportions of the mixture and well defined concentrations of protein in the water are complied with. The SAH may be used as protein. The presence of Arlacel is not required. It must be added that these emulsions may be kept at +4° for several days or easily put again in emulsion form in a syringe to be injected.

(2) Pharmacological properties of the emulsion according to the invention (a) Demonstration of the adjuvant properties of the emulsion according to the invention In the experiments which follow, the increase of the immunizing response to an antigen has been demonstrated by comparing the incomplete adjuvant of Freund, the complete adjuvant of Freund and the water in groundnut oil emulsions containing different adjuvant preparations. The adjuvant fractions used have been either, as in the complete adjuvant of Freund, entire mycobacterial cells (*Mycobacterium smegmatis*), the purified cell walls of Mycobacteria, or an isolated liposoluble preparation of *Mycobacterium tuberculosis*, for example wax D or cord factor extract of the Peurois strain, or a previously described water-soluble adjuvant prepared by synthesis, the muramyl-dipeptide mentioned above.

The antigens used were SAB, ovalbumin or an influenza vaccine, the latter sold under the name MUTA-GRIP (Pasteur Institute).

The SAB or ovalbumin in physiological solution was injected either alone or in various emulsions. The emulsions made by means of a POTTER mixer at 2000 rpm were made in the following proportions: for the preparations based on mineral oil, the ratio water to oil is 1/1, for those based on vegetable oil (groundnut oil) this ratio is 1/3 (in the latter case the antigen is also the stabiliser of the emulsion). Before emulsification the insoluble adjuvants are suspended in the oil, the liposoluble fraction dissolves in the oily phase and the water-soluble preparation in the antigen solution.

When the influenza vaccine is the antigen, the stability of the emulsion was obtained by the addition to the physiological solution containing the vaccine of 50 mg/ml of the fraction of the serum proteins of mice soluble in ammonium sulphate representing a third of that required for saturation.

The experiments were made on the mouse and the rat.

Experiments made on the mouse

The mice are Swiss females ages 2 months coming from the stock farm of the C.N.R.S.(Orléans). They are distributed in lots of 9.

Response to the SAB

On day 0, they received by the plantar method 500 μg of SAB in a volume of 0.05 ml of the various emulsions described above. The dose of adjuvant preparation per mouse is 200 μg (the doses of all the preparations are expressed in dry weight) except in an experiment where variable doses of liposoluble fraction (wax D or cord factor) were administered.

On day 17 or 30, an adjustment of 100 μg of SAB in physiological solution is effected also by plantar administration.

The mice are bled at the tail each week, then 4 days after the adjustment and 6 days after the latter they are killed by bleeding from the abdominal aorta.

Experiments made on the rat

The animals used are Lewis males of 250 g, coming from the stock farm of the C.N.R.S.(Orléans). They are distributed in lots of 7.

On day 0, they receive by plantar administration 1 mg of ovalbumin in 1 volume of 0.1 ml of the preparations previously described. The adjuvants are administered in a dose of 500 μg.

And adjustment of 100 μg antigen is given on day 35. Weekly bleeding at the tail is effected and the animals are killed on day 42 by bleeding of the abdominal aorta.

Estimation of the strength of the antibody (1) Anti-SAB or anti-ovalbumin

Passive hemagglutination.

To the series of dilutions of the serums to be tested is added a constant quantity of red corpuscles of sheep marked by the SAB or ovalbumin according to the type of the serum. The titres of the serums are expressed by the inverse of the greatest dilution causing agglutination of the red blood corpuscles.

For the intermediate bleeding, the dosages are made on the mixture of the serums (per lot). For the last bleeding, the titres of each lot represent the mean of the dosages effected on the separate serums.

"Antigen binding capacity"

The capacity of the serums to fix the SAB is measured by means of SAB marked at 125 I according to the Farr method described in the publication of P. Minden and S. Farr entitled "Method of measuring with ammonium sulphate of the capacity of fixation of the antigens", Handbook for Exp. Immunol" ed. D. M. Weir Blackwell Scientific Publications, Oxford and Edinburgh, 1967 pages 463-492. The results are expressed by the inverse of the maximum dilution capable of precipitating 33% of the antigen added.

(2) Anti-influenza vaccine

Antibody inhibiting the agglutination of the blood corpuscles of avian erythrocytes by the influenze A virus: the dosage is effected by adding growing dilutions of serum and 4 doses of hemagglutinants of influenza virus. After incubation, the desired quantity of chicken erythrocytes is added. One notices the dilution which inhibits completely the agglutination of the red corpuscles.

Result of the dosages (1) Immunization by SAB or ovalbumin.

Tables 1 and 2 give the antibody titres obtained with the mouse. By comparison with the control lot, having received the antigen alone, it is seen that important increases of the immunological response are obtained in all the lots immunized by the adjuvant preparations administered in emulsion and that, at the time of the secondary response, after the adjustment, following a first injection of groundnut oil, the level attained by the amount of antibodies is equivalent to that observed in the lots having received the mineral oil.

A notable effect is obtained in the presence of emulsion based on groundnut oil alone, on the other hand the adjuvant activity of the purified cell walls cannot be revealed if they are administered in suspension in the vegetable oil.

Immunization by the influenza virus.

The results given in Table 4 show that the preparations obtained by incorporating either the liposoluble fraction (cord factor or wax D) or the purified cell walls in the groundnut oil have an adjuvant effect greater than the adjuvant of Freund. They illustrate further the possibility of using serum proteins of the same species to obtain a stable and effective emulsion.

(b) Tolerance of water-in-vegetable oil emulsion: absence of arthrogenicity and polyarthrogenicity in the Lewis rat When administered in the paw, in suspension in the Freund incomplete adjuvant, entire cells or the mycobacterial cell walls as well as the waxes D of certain strains induce in the Lewis rat at the injection level an arthritis which can be generalized in the form of an adjuvant polyarthritis considered by some people as an autoimmune disease.

In the Lewis rat we have compared the arthrogenic activity of the mycobacterial cells and of the liposoluble fraction by injecting them either in the Freund incomplete adjuvant, or in the groundnut oil.

The animals used are male Lewis rats of 250 g provided from the stock farm of the C.N.R.S.(Orleans).

The preparations of mycobacterial origin are the following: entire cells, walls of *Mycobacterium smegmatis*. The liposoluble fraction used in the experiments was extracted from *M. tuberculosis* (Peurois strain).

The doses of all the preparations are expressed in dry weight. All the preparations were suspended in the Freund incomplete adjuvant or the vegetable oil and injected in the right hind plantar pad in a volume of 0.1ml. the animals are weighed and their paws examined on days 0, 7 and 14.

The animals are killed on day 21 and the hind paws are weighed. The severity of the arthritis is expressed by the difference in weight between the injected paw and the non-injected paw, as well as by the general signs of inflammation at the front paws and the tail.

The results recorded in Table 5 confirm that although the entire cells of *M. smegmatis* administered in the incomplete adjuvant of Freund induce a strong arthritis and a considerable polyarthritis detectable from the 14th day, these same preparations, injected in vegetable oil, cause neither arthritis nor adjuvant polyarthritis in the Lewis rat.

The tests of adjuvanticity carried out on the mouse and the rat show that it is possible to obtain an adjuvant effect equivalent to that of the freund adjuvant on using assimilatable vegetable oil as a vehicle for insoluble (entire cells), lipo-soluble or water-soluble mycobacterial preparations. For that, it is necessary to use it according to the precise experimental circumstances which allow stable emulsions to be obtained.

It must be noted that the vegetable oil, without the addition of agents such as Arlacel, is emulsifiable and that the emulsion can be stabilised by the addition of homologous proteins of the species to be immunised, as is shown by the results obtained with the influenza vaccine given on Table 4.

The experiments for studying the production of polyarthritis in the Lewis rat show that a difference exists between the emulsion based on mineral oil and that based on vegetable oil. In fact, preparations based on mineral oil are capable of inducing a considerable local inflammation and a generalized arthritis in the rat. This is not the case with the preparations based on vegetable oil.

Thus a pharmaceutical medium of great value is obtained as well as new pharmaceutical preparations which permit an effective association of the active principles of vaccines with adjuvants known for their efficiency, but the employment of which in medicaments to be used in human or veterinary therapeutics was not always easy.

The invention applies to the strengthening of the immunizing defenses of man or animal with regard to a wide variety of antigens. There may be mentioned by way of example the application of the invention to vaccines based on attenuated mycobacteria of the BCG type and vaccines against malaria. The invention also applies the vaccines intended to prevent viral maladies, for example, foot and mouth disease, viral or parasitic hepatitis for example bilharziosis.

The administration of the medicaments thus produced is preferably made by subcutaneous or intramuscular injection. It is also considered for oral application.

Table 1

Immunological response of mice immunized by SAB with different mycobacterial preparations in preparations based on mineral or vegetable oils.

| Vehicle | Adjuvant Each preparation of a dose of 200 μg | Proportion of antibody (dilution of the serum) | | | | | | | |
|---|---|---|---|---|---|---|---|---|---|
| | | Day 7 | | Day 14 | | Day 17 | Day 21 | Day 24 | |
| | | HAP[x] | ABC | HAP | ABC | ment | HAP ABC | HAP | ABC |
| Physiological solution | — | <3 | <20 | <3 | <20 | | <3 <20 | <3 | <20 |
| Composition Based on Mineral Oil + | M. tub S. peurois | <3 | <20 | 6 | 65 | | 50 200 | 800 | 800 |
| | liposoluble fraction M. smeg. smeg. puri- | 6 | 24 | 800 | 700 | | 1600 500 | 3200 | 4000 |
| | fied cell walls | 3 | 27 | 50 | 190 | | 800 800 | 1600 | 200 |
| Composition Based on Vegetable Oil φ | — | <3 | 20 | <3 | 37 | | 50 60 | 800 | 200 |
| | M. tub. S. peurois liposoluble fraction | 200 | 50 | 50 | 340 | | 400 250 | 3200 | 950 |
| | M.smeg.purified cell walls | 200 | 70 | <3 | 170 | | 200 200 | 1600 | 2300 |
| | Control M. smeg. purified cell walls without emulsion | <3 | 20 | <3 | 27 | | <3 <20 | 2 | 50 |

9 mice per lot receive in the right hind pad 500 μg of SAB in the appropriate mixture.
+Emulsion made with 1 volume of physiological solution, and 1 volume of incomplete adjuvant of Freund.
φ Emulsion made with 1 volume of physiological solution, 3 volumes of groundnut oil, except for the last lot where the antigen and the adjuvant are suspended in groundnut oil without emulsion.
[x]HAP = passive hemagglutination
t ABC = "antigen binding capacity"
* Adjust of 100 μg of SAB.

Table 2

Immunological response of mice immunized by SAB with different mycobacterial preparations in preparations based on mineral or vegetable oils

| Vehicle | Adjuvant Each preparation at a dose of 100 g | Proportion of antibody (dilution of the serum) | | | | | | | |
|---|---|---|---|---|---|---|---|---|---|
| | | Day 7 | | Day 14 | | Day 30 Adjustment | Day 34 | | Day 36 |
| | | HAP | ABC | HAP | ABC | | HAP | ABC | HAP ABC |
| Physiological Solution | — | <3 | <20 | 6.25 | 45 | | <3 | <20 | <3 <20 |
| Composition Based on Mineral Oil + | M. smeg. purified cell walls | <3 | <20 | 100 | 350 | | 800 | 1400 | 2300 2500 |
| | | <3 | <20 | 100 | 270 | | 800 | 750 | 1750 1600 |
| Composition Based on Vegetable Oil φ | — | <3 | <20 | 12.5 | 45 | | 25 | 45 | 560 400 |
| | M. smeg purified cell walls | <3 | <20 | 25 | 170 | | 100 | 280 | 1050 1000 |
| | M. tub. S. pevrosis liposoluble | <3 | <20 | 50 | 140 | | 100 | 270 | 1300 800 |

Table 2-continued

Immunological response of mice immunized by SAB with different mycobacterial preparations in preparations based on mineral or vegetable oils

| Vehicle | Adjuvant Each preparation at a dose of 100 g fraction | Proportion of antibody (dilution of the serum) | | | | | | | |
|---|---|---|---|---|---|---|---|---|---|
| | | Day 7 | | Day 14 | | Day 30 Adjustment | Day 34 | | Day 36 | |
| | | HAP | ABC | HAP | ABC | | HAP | ABC | HAP | ABC |

9 mice per lot receive in the right hind pad 500 µg of SAB in the appropriate mixture.
+ Emulsion made with 1 volume of physiological solution, and 1 volume of incomplete adjuvant of Freund.
φ Emulsion made with 1 volume of physiological solution, and 3 volumes of groundnut oil.
x HAP = passive hemagglutination.
t ABC = "antigen binding capacity"
° Adjustment of 100 µg of SAB.

Table 3

Antibody response of the Lewis rats after plantar administration of ovalbumin in emulsion with the mycobacteria in compositions based on mineral or vegetable oils.

| | Day 7 | Day 21 | Day 35 Adjustment° | Day 42 |
|---|---|---|---|---|
| | HAP$^x$ | HAP | HAP ment° | HAP |
| Composition based on mineral oil$^+$ + *M. smeg*.entire cells 500 µg | 50 | <3 | | 12,800 |
| Composition based on vegetable oil φ + *M. smeg*.entire cells 500 µg | 25 | <3 | | 7,400 |

7 animals per lot receive 1 mg of ovalbumin in the right plantar pad.
$^+$Emulsion made with 1 volume of physiological solution and 1 volume of incomplete adjuvant of Freund.
φEmulsion made with 1 volume of physiological solution and 3 volumes of groundnut oil.
$^x$HAP = passive hemagglutination of red blood corpuscles.
*Adjustment of 100 µg of ovalbumin.

Table 4

Antibody inhibiting hemagglutination in mice vaccinated with influenza virus (Mutagrip) in preparations based on mineral or vegetable oils.

| | | dose | Proportions of antibody (dilution of the serum) | | day 15 Adjustment | |
|---|---|---|---|---|---|---|
| Physiological solution | — | — | neg. | Neg. | 50 | 50 |
| Composition Based on Mineral Oil + | — | — | neg. | 12.5 | 50 | 200 |
| Composition Based in Vegetable Oil Δ | — | — | neg. | neg. | 25 | 50 |
| | M tuberculosis S. peurois liposoulbe fraction | 50 | neg. | 12.5 | 200 | 200 |
| | M. smegmatis purified cell walls | 100 | neg. | 12.5 | 100 | 400 |

9 mice per lot receive by intraperitoneal injection on day 0
50 units of Mutagrip in the appropriate mixture and on day 15
50 units of Mutagrip alone.
+Emulsion made with 1 volume of physiological solution and 1 volume of incomplete adjuvant of Freund.
ΔEmulsion made with 1 volume of physiological solution (containing 60 mg/ml of serum protein of mice) and 3 volumes of groundut oil.

Table 5

Production of adjuvant polyarthritis in the Lewis rat after injection of various mycobacterial preparations suspended in the incomplete adjuvant of Freund or groundnut oil.

| Vehicle | Adjuvant Each preparation at a dose of 500 µg | Severity of the arthritis | | | | Weight of the paws 21) | | |
|---|---|---|---|---|---|---|---|---|
| | | Day 14 | | Day 21 | | injected | non injected | difference |
| | | Arth. + | PA° A | Arth. | PAA | | | |
| Incomplete Adjuvant | — | ± | — | 0 | — | 2.68 | 2.10 | 0.58 |
| | *M. smeg.* entire cells | +++++ | ++ | +++++ | ++++ | 3.67 | 2.61 | 1.06 |
| | *M.tub.S. peurois* liposoluble fraction | ++ | — | ++ | — | 3.18 | 2.01 | 1.17 |
| | *M. smeg.* entire cells | ± | — | ± | — | 2.41 | 2.07 | 0.30 |
| Groundnut | *M. tub. S. peurois* | | | | | 2.5 | 1.97 | 0.50 |

Table 5-continued

Production of adjuvant polyarthritis in the Lewis rat after injection of various mycobacterial preparations suspended in the incomplete adjuvant of Freund or groundnut oil.

| Vehicle | Adjuvant Each preparation at a dose of 500 μg | Severity of the arthritis | | | | Weight of the paws 21) | | |
|---|---|---|---|---|---|---|---|---|
| | | Day 14 | | Day 21 | | injected | non injected | difference |
| | | Arth. + | PA° A | Arth. | PAA | | | |
| oil | liposoluble | + | − | ± | − | | | |

7 rats per lot receive 0.1 ml of oily suspension in the right hind pad.
+ Estimation of the degree of inflammation of the injected paw.
° Estimation of the degree of generalization at the 4 paws and at the tail.

We claim:

1. A stable, injectable, liquid composition for use in medical therapy of a water-in-oil emulsion of a metabolizable vegetable oil and water, the emulsion containing less water than oil and a non-immunogenic stabilizing protein in a quantity suitable to ensure the stability of the emulsion, which protein is non-toxic and metabolizable.

2. The composition of claim 1 wherein there are from about 2 to about 6 volumes of water per 10 volumes of vegetable oil.

3. The composition of claim 1 which is a pharmaceutical composition further comprising a vaccinating antigen in solution or suspension.

4. The composition of claim 1 wherein there is also present an adjuvant agent.

5. The composition of claim 4 wherein the adjuvant agent is water soluble, the principal constituent being bacterial peptidoglycan, a fragment of peptidoglycan or N-acetyl-L-alanyl-D-isoglutamine or an analog thereof.

6. The adjuvant composition of claim 4 wherein (a) there are from about 2 to about 6 volume of water per 10 volumes of vegetable oil and a non-immunogenic stabilizing protein in a quantity suitable to insure the stability of the emulsion, and (b) a water soluble adjuvant agent, the principal constituent of which is formed of peptidoglycan, or by N-acetyl-muramyl-L-alanyl-D-isoglutamine or an analog thereof.

7. The composition of claim 3 wherein there are from about 2 to about 6 volumes of water per 10 volumes of vegetable oil.

8. The composition of claim 4 wherein there are from about 2 to about 6 volumes of water per 10 volumes of vegetable oil.

9. Emulsion according to claim 1 wherein the protein is in dissolved form in the aqueous phase.

10. The composition of claim 1 wherein there are from about 30 mg to about 150 mg of protein per milliliter of aqueous phase.

11. The composition of claim 3 wherein there are from about 30 mg to about 150 mg of protein per milliliter of aqueous phase.

12. The composition of claim 4 wherein there are from about 30 mg to about 150 mg of protein per milliliter of aqueous phase.

13. The composition of claim 1 wherein the vegetable oil consists of groundnut oil, olive oil or sesame oil.

14. The composition of claim 2 wherein the protein is of human or animal origin.

15. The composition of claim 14 wherein the protein is of the serum albumin or globulin extracts of human or animal blood of the plasma or placenta.

16. The composition of claim 1 which is isotonic.

17. The composition of claim 7 wherein the protein is of human or animal origin.

18. The adjuvant composition of claim 8 wherein the protein is of human or animal origin.

19. A kit comprising a container having the metabolizable vegetable oil therein and (2) a container having the protein in a physiological serum, the vegetable oil and protein being defined in claim 1.

20. The kit assembly of claim 19 wherein the protein and the physiological serum are in separate containers.

21. The composition of claim 1 wherein the protein is soluble in the aqueous phase.

22. A kit which comprises a stable injectable composition suitable for use in medical therapy of a water-in-oil emulsion of a metabolizable vegetable oil and a non-immunogenic stabilizing protein in a quantity suitable to ensure the stability of the emulsion, which protein is non-toxic and metabolizable, and an adjuvant, said emulsion and said adjuvant being initially held out of contact with each other but capable of being intermixed to form the injectable composition.

23. The kit of claim 22 which further comprises a vaccinating antigen intermixed with the composition.

24. The composition of claim 22 wherein the protein is soluble in the aqueous phase.

25. A liquid injectable stable vaccine composition comprising a water-in-oil emulsion of metabolizable vegetable oil in an aqueous solution containing a non-immunogenic stabilizing protein, a water soluble adjuvant agent and a vaccinating antigen, there being less water than oil.

26. The liquid injectable stable vaccine composition of claim 25 wherein there are from about 2 to about 6 volumes of water per 10 volumes of vegetable oil.

27. The liquid injectable stable vaccine composition of claim 26 wherein the protein is an animal or human protein.

28. The liquid injectable stable vaccine composition of claim 27 wherein the protein is of the serum albumin or globulin extracts of human or animal blood of the plasma or placenta.

29. The vaccine composition of claim 25 wherein the adjuvant has as its principal constituent bacterial peptidoglycan or fragments thereof, of an N-acetylmuramyl-L-alanyl-D-isoglutamine or an analog thereof.

30. The composition of claim 26 wherein the adjuvant has as its principal constituent bacterial peptidoglycan or fragments thereof, or an N-acetyl-muramyl-L-alanyl-D-isoglutamine or an analog thereof.

31. A stable, injectable liquid adjuvant composition suitable for use in medical therapy which comprises: a water-in-oil emulsion having from about 2 to about 6 volumes of water per 10 volumes of metabolizable vegetable oil and from about 30 mg to about 150 mg of non-immunogenic stabilizing protein of human or animal origin per milliliter of water, which protein is non-toxic and metabolizable, and an adjuvant of the water soluble fraction type, the principal constituent of which is bacterial peptidoglycan, or a fragment thereof, or N-acetyl-muramyl-L-alanyl-D-isoglutamine or an analog thereof.

32. The composition of claim 31 wherein the protein is soluble in the aqueous phase.

* * * * *